(12) United States Patent
Gorsek

(10) Patent No.: US 6,572,899 B1
(45) Date of Patent: Jun. 3, 2003

(54) MEMORY LOSS TREATMENT FORMULATION

(75) Inventor: Wayne F. Gorsek, Boynton Beach, FL (US)

(73) Assignee: Vitacost.Com, Inc., Boynton Beach, FL (US)

( * ) Notice: Subject to any disclaimer, the term of this patent is extended or adjusted under 35 U.S.C. 154(b) by 0 days.

(21) Appl. No.: 10/187,615

(22) Filed: Jul. 3, 2002

(51) Int. Cl.⁷ .................. A01N 65/00; A61K 35/78
(52) U.S. Cl. .................. 424/732; 424/725; 424/752
(58) Field of Search .................. 424/725, 752, 424/732

(56) References Cited

U.S. PATENT DOCUMENTS 6,368,617 B1 * 4/2002 Hastings et al. ............ 424/439
6,436,946 B1 * 8/2002 Mann ........................ 424/752

* cited by examiner

*Primary Examiner*—Herbert J. Lilling
(74) *Attorney, Agent, or Firm*—Hoffman, Wasson & Gitler, PC

(57) ABSTRACT

The invention relates to a composition that contains the most potent combination of nutrients which have been focused to assist in the struggle with memory loss, dementia and Alzheimers disease.

2 Claims, No Drawings

MEMORY LOSS TREATMENT FORMULATION

BACKGROUND OF THE INVENTION

The invention relates to a composition that contains the most potent combination of nutrients which have been focused to assist in the struggle with memory loss, dementia and Alzheimers disease.

The advanced formulation is designed to promote healthy memory and provide optimal neuro protection.

Many studies have been conducted in Europe and in the United States on the effects of individual natural supplements on the brain and the advanced memory formulation embodied by the crucial combinations of ingredients has proven very promising in maintaining healthy memory and providing optimal neuro protection.

It is an object of the present invention to provide an unique and superior formulation which allows individuals improve, maintain and enhance memory. It is also a design to prevent and treat dementia and Alzheimers disease.

SUMMARY OF THE INVENTION

The key to the unique formulation is a combination of specific vitamins, minerals, herbs and nutrients. These essential components in the amounts provided uniquely contribute to improved memory and neuro health maintenance.

The formulation contains Phosphatidylserine, Phosphatidylcholine, CoEnzyme Q10, Alpha Lipoic Acid, Vinpocetine, Acetyl-L-Carnitine, Ginkgo Biloba, Blueberry and Spinach extracts, as well as other ingredients and healthy filler ingredients.

The formulation is preferably delivered in capsule form at 8 capsules per day.

DETAILED DESCRIPTION OF THE INVENTION

The present invention involves a composition for oral ingestion that contains Phosphatidylserine, Phosphatidylcholine, CoEnzyme Q10, Alpha Lipoic Acid, Vinpocetine, Acetyl-L-Carnitine, Ginkgo biloba, Blueberry and Spinach extracts, as well as other ingredients and healthy filler ingredients. More specifically, this formulated product is a memory loss and memory enhancement management formulation. This formulation allows for enhanced maintenance of memory and prevention of loss.

In order to secure the desired result the following essential components are provided:

Acetyl-L-Carnitine (ALC) is an important ingredient to enhance mental quickness and has many neurogical benefits. ALC improves memory and learning, improves cerebral blood flow and elevates mood. (approximately 1000 mg)(100 mg–10,000 mg)

Standardized Ginkgo Biloba herb promotes improved memory, oxygen flow to the arms, legs, and brain by supporting strong blood circulation. (120 mg) (standardized 24% ginkgo flavon glycosides, 6% terpene lactones)(12 mg–1,200 mg)

Alpha lipoic Acid is an essential antioxidant which has free radical quenching properties. Lipoic Acid acts as a fat and water soluble antioxidant, supporting vitamins C and E at the cellular level (300 mg)(30 mg–3,000 mg).

Blueberry and Spinach extracts contain high levels of required antioxidants which promote improved cognitive abilities. (Approximately 100 mg of each) (10 mg–4,000 mg)

Phosphatidylserine(300 mg) and Phosphatidylcholine (200 mg) both are essential ingredients for memory maintenance.

CoEnzyme Q10 (60 mg) is an essential free radical scavenger for enhanced cellular energy production, that is vital for memory enhancement and maintenance (6 mg–6,000 mg).

Vinpocetine (15 mg) is an essential supplement component for a healthy memory (1.5 mg–150 mg).

Additionally, the following Vitamins, Minerals and natural supplement additives are all important for the memory health formulation:

| | Amount per serving | % daily value |
|---|---|---|
| Vitamin A (betatene ®) (as natural carotenoids beta carotene, alpha carotene, lutein, zeaxanthin, cryptoxanthin and palmitate) | 5,000 IU | 100% |
| Vitamin C (Ester C ®) (as magnesium ascorbate) | 1 g (1,000 mg) | 1,666% |
| Vitamin D3 (as cholecalciferol) | 400 IU | 100% |
| Natural Vitamin E (as d-alpha tocopherol succinate, gamma, delta and beta) | 800 IU | 2666% |
| Thiamine (vitamin B1 HCl) | 200 mg | 13,333% |
| Riboflavin (vitamin B2) | 10 mg | 588% |
| Niacin (vitamin B3) | 100 mg | 500% |
| Pyridoxine HCL (vitamin B6) | 100 mg | 5,000% |
| Folic Acid (as folacin) | 800 mcg | 200% |
| Vitamin B12 (Methylcobalamin) | 2 mg | 33,332% |
| Biotin | 2 mg | 666% |
| Pantothenic Acid (vitamin B5 as d-calcium pantothenate) | 100 mg | 1,000% |
| Magnesium (as Ascorbate) (Ester C) | 68 mg | 17% |
| Magnesium (as Citrate) | 232 mg | 58% |
| Zinc (as OptiZinc ®) | 15 mg | 100% |
| Selenium (Selenomethionine) | 200 mcg | 286% |
| Copper (as chelate) (AAC) | 1 mg | 50% |
| Manganese (as chelate) (ACC) | 1 mg | 50% |
| Chromium (as chromium polynicotinate) | 400 mcg | 333% |
| Molybdenum (as chelate) (ACC) | 150 mcg | 200% |
| Prosphatidylserine | 300 mg | |
| Phosphatidylcholine | 200 mg | ** |
| Coenzyme Q10 | 60 mg | |
| Alpha Lipoic Acid | 300 mg | |
| Black Pepper (Bioperine ®) (piper nigrum) (fruit extract) | 5 mg | ** |
| Vinpocetine | 15 mg | ** |
| Acetyl-L-Carnitine | 1 g | ** |
| Bioflaonoid (as Zuercetin) | 100 mg | ** |
| Red Wine Extract (Standardized 30% polyphenols) | 100 mg | |
| Green Tea Extract (standardized 98% polyphenols) 80% Catechins, 45% EGCG) | 100 mg | |
| Pomegranate Extract (Standardized for 70% Ellagic acid) | 60 mg | ** |
| Inositol | 50 mg | ** |
| Inositol (as Hexaniacinate) | 100 mg | |
| Ginkgo Biloba | 120 mg | ** |
| Lutein Extract (from 120 mg FloraGLO ®) | 6 mg | ** |
| Lycopene (from 100 mg Lyc-O-Mato ®) | 5 mg | ** |
| Trimethylglycine (Betaine HCL) | 50 mg | ** |
| Blueberry Extract | 100 mg | ** |
| Spinach Leaf Extract | 100 mg | ** |
| (other ingredients: Silica, Cellulose, | | ** |

| | Amount per serving | % daily value |
|---|---|---|
| Magnesium Stearate, and Kosher Gelatin Capsule) | | |

In addition to the key components, other components such as kosher gelatin (capsules), magnesium stearate and silica and cellulose are included.

Although the invention has been described primarily in connection with special and preferred embodiments, it will be understood that it is capable of modification without departing from the scope of the invention. The following claims are intended to cover all variations, uses, or adaptations of the of the invention, following, in general the principles thereof and including such departures from the present disclosure as come within known or customary practice in the field to which the invention pertains, or as are obvious to persons skilled in the field.

What is claimed is:

1. A Healthy memory and Neuro protection composition comprising an effective amount of:

Acetyl-L-Carnitine;

Ginkgo Biloba;

Alpha Lipoic Acid;

Blueberry Extract comprising high levels of antioxidants which promote improved cognitive abilities;

Spinach extract comprising high levels of antioxidants which promote improved cognitive abilities;

CoEnzyme Q10;

Phosphatidylserine; and

Phosphatidylcholine.

2. A Healthy memory and Neuro protection composition as claimed in claim 1 comprising an effective amount of:

1000 mg Acetyl-L-Carnitine;

120 mg Ginkgo Biloba;

300 mg Alpha Lipoic Acid;

100 mg Blueberry Extract;

100 mg Spinach extract;

15 mg Vinpocetine;

60 mg CoEnzyme Q10;

300 mg Phosphatidylserine; and 200 mg Phosphatidylcholine.

* * * * *